United States Patent [19]
Constantinides

[11] Patent Number: 6,090,050
[45] Date of Patent: Jul. 18, 2000

[54] THERMOMETRIC APPARATUS AND METHOD

[75] Inventor: George P. Constantinides, San Antonio, Tex.

[73] Assignee: Salix Medical, Inc., San Antonio, Tex.

[21] Appl. No.: 09/116,890

[22] Filed: Jul. 16, 1998

[51] Int. Cl.[7] .................................................. A61B 5/00
[52] U.S. Cl. .................... 600/549; 600/474; 374/100; 374/112; 374/142
[58] Field of Search ................... 600/473, 474, 600/475, 549, 587, 592; 374/15, 45, 54, 100, 104, 112, 121, 142

[56] References Cited

U.S. PATENT DOCUMENTS

| | | | |
|---|---|---|---|
| 3,651,694 | 3/1972 | Lamb | 73/342 |
| 3,877,463 | 4/1975 | Cary et al. | 128/2 H |
| 4,173,970 | 11/1979 | Momin | 128/736 |
| 4,306,569 | 12/1981 | Weil et al. | 600/549 |
| 4,379,461 | 4/1983 | Nilsson et al. | 128/736 |
| 4,572,213 | 2/1986 | Kawahara | 600/549 |
| 4,636,091 | 1/1987 | Pompei et al. | 374/124 |
| 4,797,840 | 1/1989 | Fraden | 364/557 |
| 4,854,730 | 8/1989 | Fraden | 374/164 |
| 4,874,253 | 10/1989 | Pompei et al. | 374/121 |
| 4,993,419 | 2/1991 | Pompei et al. | 128/664 |
| 5,012,813 | 5/1991 | Pompei et al. | 128/664 |
| 5,017,019 | 5/1991 | Pompei | 600/549 |
| 5,062,248 | 11/1991 | Kunert | 52/208 |
| 5,088,493 | 2/1992 | Giannini et al. | 128/633 |
| 5,174,656 | 12/1992 | Dotan | 600/549 |
| 5,183,337 | 2/1993 | Pompei | 374/2 |
| 5,199,436 | 4/1993 | Pompei et al. | 128/664 |
| 5,247,940 | 9/1993 | Wilk | 128/736 |
| 5,271,407 | 12/1993 | Pompei et al. | 128/664 |
| 5,325,863 | 7/1994 | Pompei | 128/736 |
| 5,370,114 | 12/1994 | Wong et al. | 128/633 |
| 5,381,796 | 1/1995 | Pompei | 128/664 |
| 5,419,321 | 5/1995 | Evans | 128/633 |
| 5,452,725 | 9/1995 | Martenson | 600/549 |
| 5,596,987 | 1/1997 | Chance | 128/633 |
| 5,666,956 | 9/1997 | Buchert | 128/664 |
| 5,678,566 | 10/1997 | Dribbon | 128/779 |
| 5,803,915 | 9/1998 | Kremenchugsky et al. | 600/549 |
| 5,820,263 | 10/1998 | Ciobanu | 600/549 |
| 5,893,833 | 4/1999 | Pompei et al. | 600/549 |
| 5,897,505 | 4/1999 | Feinberg et al. | 600/549 |

OTHER PUBLICATIONS

Francisco Pompei, et al. *Physicians Reference Handbook on Temperature: Vital Sign Assessment with Infrared Thermometry.* pp. 140–158, Exergen Corporation, Boston, MA., 1996.

Mary Beth Dorgan, PT, et al. *Performing Foot Screening for Diabetic Patients,* Amputation of a lopwer limb is a devasting complication for patients with diabetes. Effective prevention begins with competent assessment and patient education. pp. 32–37, Nov. 1995.

Harry T. Bergtholdt, MS Temperature Assessment of the Insensitive Foot. Physical Therapy, v. 59 No. 1, pp. 18–22, Jan. 1979.

Harry T. Bergtholdt, M.S. et al. Thermography: An Aid in the Management of Insensitive Feet and Stumps. Arch Phys Med Rehabil, v. 56, pp. 205–209, May 1975.

*Primary Examiner*—Cary O'Connor
*Assistant Examiner*—Charles Marmor, II
*Attorney, Agent, or Firm*—Jenkens & Gilchrist, P.C.

[57] ABSTRACT

A thermometric apparatus useful for recording temperatures, after sensing contact with, or proximity to, a dermal surface is disclosed. The apparatus also provides various visual and aural mechanisms for indicating alarm conditions to the user. A method for thermometric diagnosis using temperatures acquired from bilateral dermal surfaces is also disclosed. The apparatus and method are especially useful in the early diagnosis of plantar foot surface pre-ulceration conditions which may be present in diabetic persons.

35 Claims, 4 Drawing Sheets

THERMOMETRIC APPARATUS AND METHOD

BACKGROUND OF THE INVENTION

1. Technical Field

This invention relates generally to the field of thermometric diagnostic devices and methods, and more particularly, to an apparatus and method for sensing, recording, and indicating thermal irregularities across a dermal surface.

2. History of Related Art

Foot problems are the major cause of amputation and physical disability in patients with diabetes. Yet studies have shown that simple techniques such as identifying patients at risk for foot ulcers and educating these patients about proper foot care can help prevent such serious complications.

Preventing diabetic foot problems requires careful monitoring of the patient's feet on a regular basis. Unfortunately, the daily inspection of the plantar and dorsal surfaces of the feet require some manual dexterity and experience, and some patients may be hampered in their ability to conduct regular inspections because of obesity, arthritis, or poor eyesight. Often, mirrors or teaching a friend or family member to conduct the inspection are required.

In addition, a necessary component in the causal pathway to foot complications in persons with diabetes is peripheral sensory neuropathy. Damage to sensory feedback concerning position and tactile stimulation of the foot provides an environment where skin, ligaments, or bones of the foot can be injured without any knowledge by the patient that such injury has occurred. For instance, areas of high pressure on the sole of the foot normally become irritated and inflamed because of normal walking activities. Persons with normal pain sensation will stop or modify their activities to avoid pain and subsequent ulceration, or other damage. However, in diabetics with nerve damage the sensation of pain is often absent, and activities are often continued until the injury is so prominent that amputation is required.

Degenerative arthritis, bunion deformities, or hammer toes, as well as other foot deformities, increase the risk of developing an ulcer on the foot. Such physical alterations in the structure of the foot can produce high pressure areas, which in turn produce inflammation, tissue destruction, and ulceration. Once again, without the early warning signal provided by normal pain sensation, tissue damage may become quite advanced before reaching a level noticed by the patient. Unfortunately, by the time that such knowledge occurs, amputation may be required.

Prevention and treatment of ulceration can be quite effective in preventing lower extremity amputation in diabetics. Prevention strategies focus on protecting the sole of the foot from high pressure areas, and detection of early signs of tissue injury. Objective methods of implementing these strategies, which often involve measurement of inflammation and foot pressures, have historically been expensive, bulky, or relatively unavailable to physicians and their patients. However, it has been found that an increase in local skin temperature is one of the earliest indications of tissue injury or inflammation. Therefore, monitoring the skin temperature on a monthly basis by physicians and more important, on a daily basis by patients, can provide an easy, inexpensive, and readily quantifiable way to detect areas of the foot that are at risk of ulceration.

The most common method of evaluation and diagnosis for foot temperature involves manual manipulation of the feet with a single hand to find a warm area or "hot spot." The high temperature area is compared with the rest of the foot, and the corresponding bilateral location on the other foot. A temperature difference of more than 2° C. is clinically significant, and is held to be detectable by the average practitioner. However, physicians and others with temperature-insensitive hands, or circulation problems of their own may not be able to reliably detect such small changes in temperature.

Various instruments have been devised to detect skin temperature, but these are often expensive, or formed for use in the ear, or for general use, and do not lend themselves to use with the foot. The display may not be visible to the user if applied to the sole of the foot; there is also no sure way to determine sensor proximity to the foot, or provide any type of scanning function which can be monitored by the user as areas of lower or higher temperature are encountered. Finally, such devices are ordinarily constructed so as to measure the temperature of any surface encountered; whether the temperature measurement is relevant to skin, or to some other surface within the field of view of the sensor, is not detected by the instrument.

Therefore, what is needed is an apparatus and method for easily, inexpensively, and repeatedly detecting temperature differences along the sole of the foot of about 2° C. or greater. Further, such a device and method should lend themselves to continuous scanning of the surface of the sole, along with reliable determination of the presence of an anatomical surface in front of the sensing element. Such a device and method which provide both visual and audio indications or alarms to the practitioner and/or patient would also be desirable for persons hampered by poor vision or poor hearing.

SUMMARY OF THE INVENTION

In accordance with one aspect of the present invention a thermometric apparatus has: a controller; a timer electrically connected to the controller; a memory electrically connected to the controller; a means for sensing a plurality of temperatures, the temperature sensing means being electrically connected to the controller, the temperature sensing means acting to convert a plurality of temperatures to a corresponding plurality of electrical signals, the controller converting the plurality of electrical signals to a corresponding plurality of temperature numeric values, said numeric values being stored in the memory; a proximity sensing means for sensing proximity to a dermal surface, the proximity sensing means being electrically connected to the controller; a speaker electrically connected to the controller; and a display electrically connected to the controller. The controller and the timer may be integrated into a single unit, and the controller and memory may be integrated into a single unit. In addition, the proximity sensing means of the thermometric apparatus of the present invention may comprise a switch activated by capacitance. The temperature sensing means of the thermometric apparatus of the present invention may comprise an infrared sensor which is inactive until the proximity sensing means senses a predetermined capacitance of greater than about 10 pF. The display of the thermometric apparatus of the present invention may comprise a series of LEDs arranged in a linear sequence, selected ones of the LEDs are colored red, yellow, and green.

The plurality of numeric temperature values may be stored into the memory within a predetermined time period (less than about 0.08 seconds) measured by the timer. After the plurality of temperature numeric values are stored into the memory and averaged by the controller to produce a first average temperature value, the resulting first average temperature value is stored in the memory. A second plurality of temperature numeric values may be stored into the memory and averaged by the controller to produce a second average temperature value, which is compared with the first average temperature value. The second average temperature value may then be displayed on the display if the difference between the second average temperature value and the first average temperature value is less than a predetermined difference of about 0.2° C. The second average temperature value is typically not displayed on the display if the difference between the second average temperature value and the first average temperature value is greater than a predetermined difference of about 0.2° C.

The temperature sensing means of the thermometric apparatus of the present invention may be electrically connected to the controller using a signal conditioner. If the plurality of electrical signals comprise unwanted frequency signals, then the signal conditioner operates to filter the plurality of electrical signals by removing the unwanted frequency signals. The plurality of electrical signals may also comprise erratic values. If so, the signal conditioner may operate to smooth the plurality of electrical signals by removing the erratic values. Also, the plurality of electrical signals may comprise noise, and the signal conditioner may operate to remove the noise.

Moreover, the temperature sensing means of the thermometric apparatus of the present invention may provide a type k thermocouple output to the signal conditioner. The temperature sensing means and the proximity sensing means may be integrated into a single sensor head which is attached to a goose-neck.

Furthermore, the plurality of temperature numeric values stored into the memory and averaged by the controller to produce a first average temperature value may be directly displayed on the display. Additionally, a second plurality of temperature numeric values stored into the memory and averaged by the controller may be used to produce a second average temperature value. The difference between the first average temperature value and the second average temperature value may then be displayed on the display. The speaker may be used to produce an audible tone whose frequency is proportional to an average value of the plurality of numeric values.

In accordance with another aspect of the present invention, a method of thermometric diagnosis comprises approaching a first bilateral dermal surface with a proximity sensing means until a first proximity signal is detected, acquiring a first temperature value of the first bilateral dermal surface after the first proximity signal is detected, approaching a second bilateral dermal surface with the proximity sensing means until a second proximity signal is detected, the second bilateral dermal surface having a one-to-one physical correspondence with the first bilateral dermal surface, acquiring a second temperature value of the second bilateral dermal surface after the second proximity signal is detected, subtracting the second temperature value from the first temperature value to produce a temperature difference, and displaying the difference on a display.

These steps may be performed repeatedly. The first bilateral dermal surface may be selected sole of a first foot, and the second bilateral dermal surface may be a selected sole of a second foot. The method may include the step of producing an audible tone whose frequency is proportional to the difference.

The method of thermometric diagnosis of the present invention may further comprise the steps of illuminating a green colored visual element when the difference is less than about 2° C., illuminating a yellow colored visual element when the difference is equal to about 2° C., and illuminating a red colored visual element when the difference is greater than about 2° C.

In accord with another aspect of the present invention, a method of thermometric diagnosis may further comprise the steps of approaching a first dermal surface with a proximity sensing means until a first proximity signal is detected, acquiring a first temperature value of a first dermal surface after the first proximity signal is detected, displaying a first temperature value on a display; approaching a second dermal surface with the proximity sensing means until a second proximity signal is detected; acquiring a second temperature value of the second dermal surface after the second proximity signal is detected, displaying a second temperature value on the display if the first temperature value is less than the second temperature value; and displaying a first temperature value on the display if the second temperature value is less than the first temperature value.

The method of thermometric diagnosis of the present invention may further comprise the steps of adding a preselected temperature value to a second temperature value to produce a high temperature value, subtracting a preselected temperature value from a second temperature value to produce a low temperature value, and emitting an audible tone whose frequency is proportional to subsequently acquired temperature values which are greater than the low temperature value and less than the high temperature value. The preselected value may be 1.0°C.

BRIEF DESCRIPTION OF THE DRAWINGS

A more complete understanding of the structure and operation of the present invention may be had by reference to the following detailed description when taken in conjunction with the accompanying drawings, wherein.

DETAILED DESCRIPTION OF PRESENTLY PREFERRED EXEMPLARY EMBODIMENTS

Figure 1:
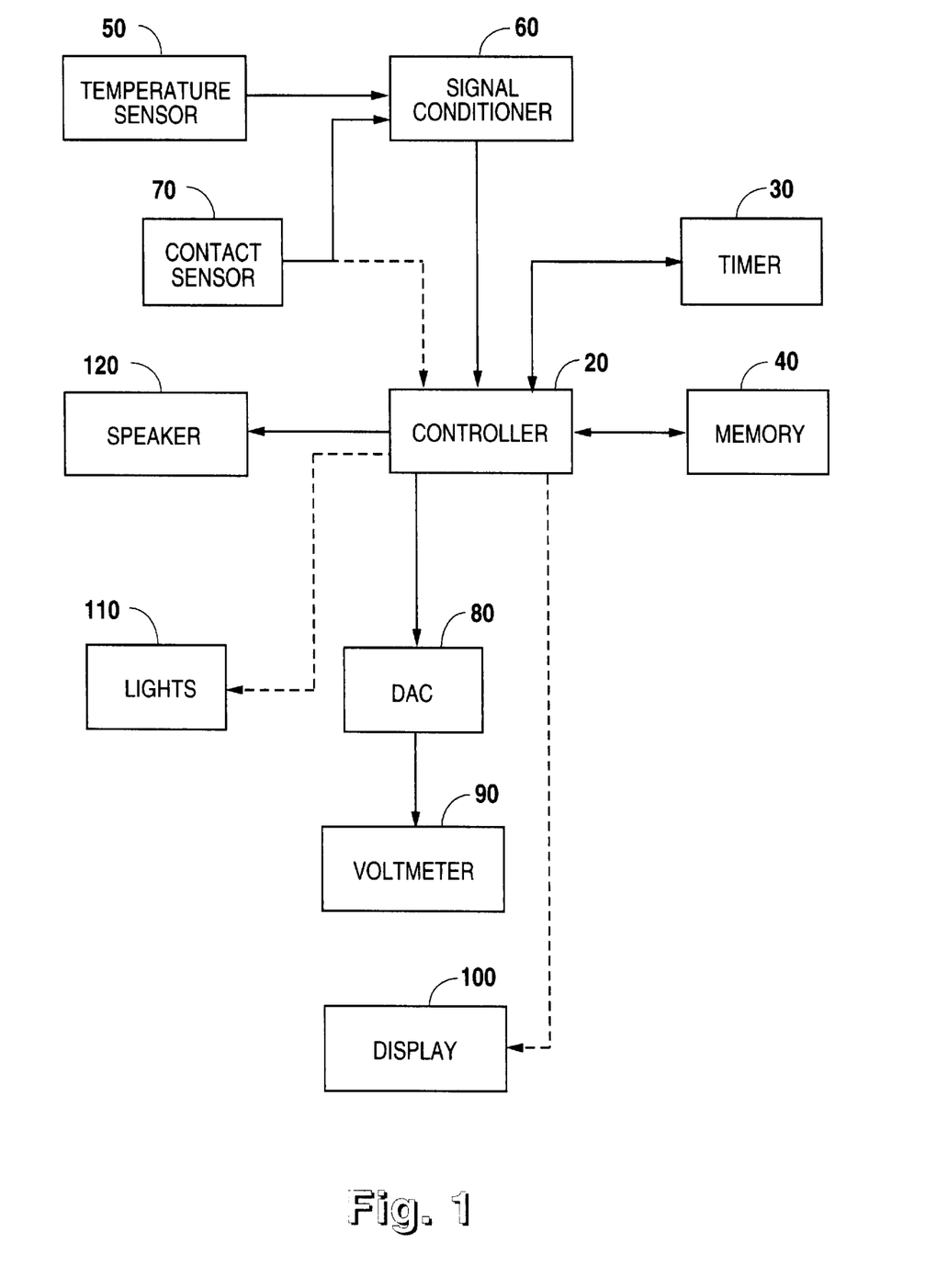
FIG. 1 is a simplified schematic block diagram of a preferred embodiment of the present invention.

Turning now to FIG. 1, a schematic block diagram of the thermometric apparatus 10 of the present invention can be seen. A controller 20, which can be similar to, or identical to a micromint PIC STIC 3 microcontroller, having a built-in, 12-bit differential analog to digital converter (ADC) is used to regulate the activity of the apparatus. Of course, any other commonly available microcontroller may be used. Preferred implementations include those controllers with built-in analog signal processing circuitry timers, memory, and display driving circuitry. For purposes of clarity, the timer 30 and memory 40 are illustrated separately from the controller 20. However, they can just as easily be combined into the controller 20 itself.

The controller 20 typically processes analog information provided by the temperature sensor 50 and the proximity sensor 70 after appropriate conditioning by the signal conditioner 60. The required signal conditioning may include smoothing, filtering, and/or noise removal, as are well known in the signal-processing art.

The temperature sensor is identical to, or similar to, an Omega OS 36-98.6F, which is an infrared temperature sensor 50 having a type k thermocouple output. The signal conditioning required by signal conditioner 60 in this case can be provided by a device similar to, or identical to, an Analog Devices AD595CQ thermocouple amplifier. The signal conditioner 60 in this case will amplify the output of the temperature sensor 50 to provide a signal magnitude which is compatible with the input of the ADC residing within the controller 20.

The proximity sensor 70 comprises a contact switch activated by the capacitance of the human body in close proximity. That is, a proximal capacitance of greater than about 10pf at the switch (i.e., proximity sensor 70) will cause the controller to sense the presence of an anatomical surface, as opposed to an inanimate presence, in close proximity to the device. Activation of the proximity sensor 70 in this fashion signals the controller 20 to begin acquisition of temperatures via the temperature sensor 50 and signal conditioner 60. In this particular implementation, there is no signal conditioning required to process the signal from the proximity sensor 70, which comprises, as mentioned above, a simple capacitance-sensitive touch switch, which is well known in the art. However, other approaches to detection of anatomic proximity may require the filtering, smoothing, and/or amplification functions of the signal conditioner 60.

The controller 20 communicates with the user of the thermometric apparatus 10 by way of visual and audio signals. That is, any number of sounds can be communicated to the user by way of speaker 120. Lights 110, which can be similar to, or identical to, LEDs, or other visual, colored indicators, can be used as an alternative to the audio output provided by speaker 120. This is especially useful for those users having minimal or nonexistent hearing capability.

A digital-to-analog converter (DAC) 80 may be used to convert digital signals from the controller 20 into analog signals appropriate to drive the voltmeter 90 for display of absolute or relative temperature values, as detected by the temperature sensor 50. For more complex implementations of the apparatus, a display 100 can be used for indicating temperatures, profiles, memorized values, etc. Such advance functions of the apparatus 10 will be described further hereinbelow.

Figure 2:
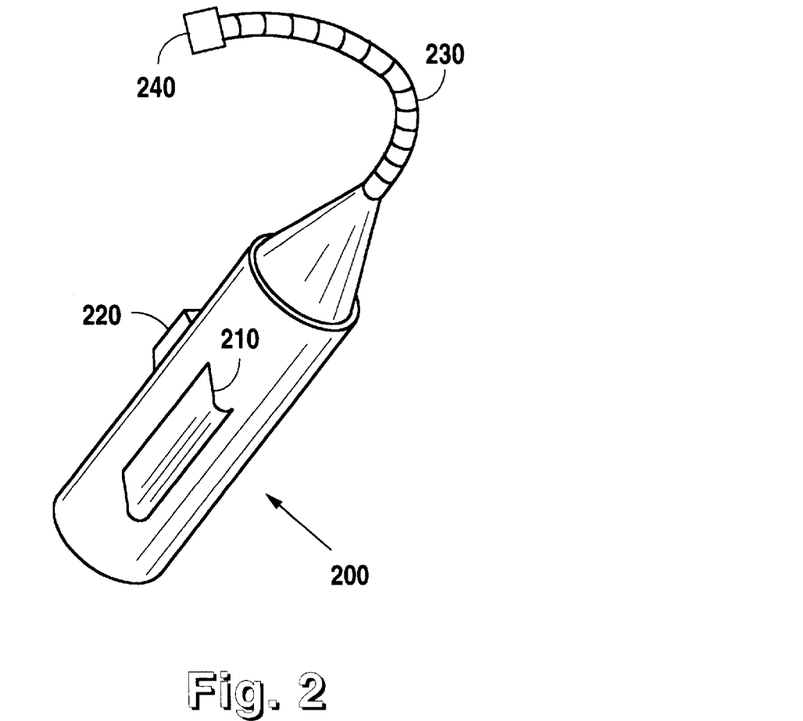
FIG. 2 is a perspective view of one embodiment of the present invention.
Figure 3:
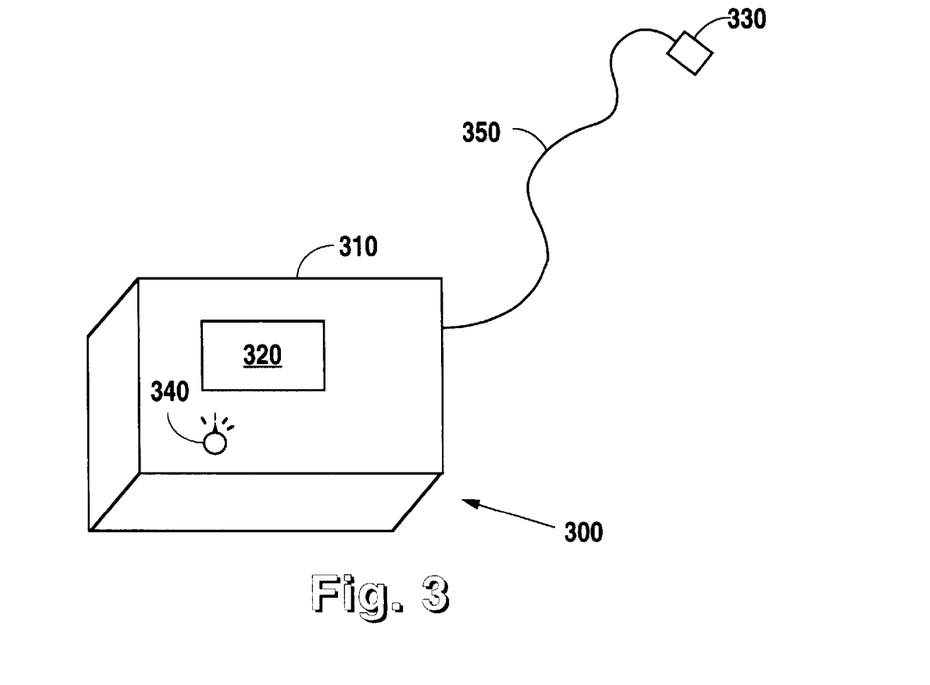
FIG. 3 is a perspective view of an alternative embodiment of the present invention.

FIGS. 2 and 3 illustrate physical packaging concepts for the thermometric apparatus 10 of the present invention. In FIG. 2, a FOOTSCAN™ device 200 can be seen. This particular implementation, which is seen as relatively inexpensive embodiment of the invention, is intended to be used on a daily basis by an individual patient to monitor foot temperature fluctuations, which are indicative of foot pathology. The FOOTSCAN™ device 200 is an easy to use, portable, hand-held device that measures the temperature anywhere on the patient's foot, particularly the sole. Its working range is from about 23.9° to about 37.8°, and it has an accuracy of about 0.3° C.

The FOOTSCAN™ device 200 is intended for rapid determination by a patient of his or her risk of potentially catastrophic foot complications. It is a hand-held instrument with a goose-neck 230 flexible shaft connecting the sensor head 240, housing the proximity sensor 70 and temperature sensor 50, to the hand-held case 250. A switch 220 is used to supply power to the device 200, while a simple display 210 is used by the patient to view the information resulting from application of the sensor head 240 to the foot.

The sensor head 240 is situated at the distal end of the goose-neck; it is applied to the sole of the foot by touching the head 240 to the foot to obtain a near instantaneous digital readout of the dermal temperature at the point of application. It should be noted that the proximity sensor 70, which permits acquisition of dermal temperatures by the temperature sensor 50, only activates when in proximity to the dermal surface. This feature assures accurate temperature measurements by eliminating spurious readings which may be obtained by accidental reading of ambient conditions, or, extraneous objects which come into the field of view of the temperature sensor 50. Further, the ergonomic design of the FOOTSCAN™ device 200 allows for ease of positioning on the dermal surface, even for those patients hampered by obesity or arthritis.

Another feature of the design includes a stabilization mechanism implemented by the controller 20 which makes use of multiple temperature readings at the same location over a short period of time (e.g. about 0.25 sec.) to obtain a stable reading. It has been determined that a tolerance of approximately 0.2° C. between scanned readings at the same location provides a useful system with repeatable and accurate measurement capability.

A typical algorithm for acquiring stable temperature readings includes repetitive acquisition of approximately ten readings, averaging the readings, and repeating the process three times within about 0.25 sec. If the difference between the maximum and minimum average values obtained is less than approximately 0.2° C., then the average of these three acquisition cycles can be displayed to the patient; otherwise, the process is repeated from the beginning. This stabilized acquisition process, or verification procedure, is useful because it ensures that temperature readings are only displayed after a steady state has been reached. If the sensor head 240 is moved too quickly across the dermal surface, the instrument will detect a widely varying temperature range, and accurate readings are not possible. The verification procedure also effectively eliminates noise in the readings.

A more advanced implementation of the apparatus of the present invention can be seen in FIG. 3. This embodiment is referred to as the RISKSCAN™ device. This particular embodiment is characterized by a case 310 which is designed to be small enough for a physician to carry in his pocket. A complex display 320 is available to present various forms of information. However, the sensor array 330 is similar to, or identical to, that used by the FOOTSCAN™ device 200. A non-rigid, flexible, cord 350 is used to connect the sensor array 330 to the balance of the RISKSCAN™ device electronics 300.

In addition to the simple temperature acquisition mode of the FOOTSCAN™ device 200, the RISKSCAN™ device 300 can also implement an isoscan mode and a soundscan mode. During use, the physician will typically select the mode using the mode switch 340 on the front panel of the RISKSCAN™ device.

Figure 4:
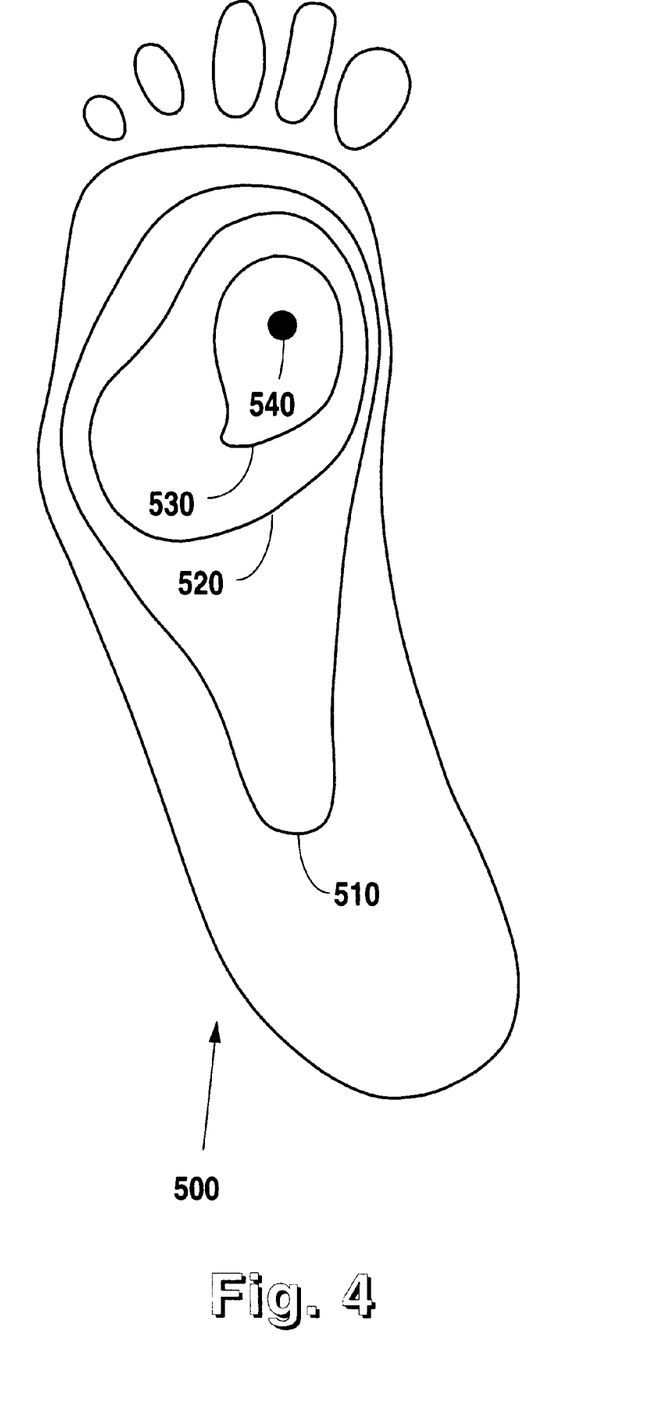
FIG. 4 is a plantar view of the right foot indicating isotherms.

In the "isoscan" mode, the RISKSCAN™ device 300 is used to determine areas of the sole which exhibit temperatures within a predetermined range of a predefined peak temperature. This feature allows measurement not only of the value and location of a single elevated temperature, but also its topographical spread along the sole. For example, as seen in the plantar view of the right foot in FIG. 4, the right foot 500 can be "mapped" by areas of first isotherm 510, second isotherm 520, third isotherm 530, and peak temperature 540. That is, the cooler temperatures of the foot sole typically approach a peak temperature as shown in the illustration. A physician will use the RISKSCAN™ device 300 to find the location of the peak temperature 540, and then activate the isoscan mode, which will indicate the topographical spread of the peak temperature 540, by means of an audible signal. The "isoscan" mode is based on the concept that temperature magnitude and its topographic location are important indications of the diabetic foot pathophysiology. The "isoscan" mode allows the physician to evaluate the effectiveness of his treatment approach; decreasing the number or size of areas having elevated temperatures indicates that the treatment approach is indeed efficacious.

In the "isoscan" mode, the physician uses the RISKSCAN™ device 300 to determine the temperature profile of the foot sole (or other skin on the body) with respect to a peak temperature value by scanning the entire area; the display 320 and memory 40 are constantly updated with temperature values that are greater than any previously shown as the sensor head is moved over the scanned area. That is, a first temperature value is obtained from the scanned area, displayed on the display 320 and stored into the memory 40. Once a second temperature value is obtained or measured, which is greater than the first temperature value, the second value is displayed on the display 320 and stored into the memory 40. The first temperature value is erased from the memory 40 and removed from the display 320. Once the physician believes that the highest value of temperature in the scanned area has been obtained for display, it is saved into the memory 40 as a peak temperature value. A high temperature value and a low temperature value are subsequently determined by adding and subtracting, respectively, one degree (or other preselected value) from the peak value and storing the calculated high temperature value and low temperature values into the memory 40. The RISKSCAN™ device 300 will then emit a sound with a frequency proportional to the sensed temperature, and no sound will be emitted whenever the currently sensed temperature value is higher than the high temperature value, or lower than the low temperature value. Of course, these high and low temperature values can be set to a preselected value of ±1.5 degrees from the peak value, or to a preselected value of ±2.0 degrees from the peak value, or to other preselected values, as determined by the program in the controller 20.

The "soundscan" mode, selected by the physician using the mode switch 340, gives an audible tone of varying frequency which is proportional to the average measured temperature at the dermal surface. This feature allows the physician to gather a mental picture of the topographic temperature distribution on the sole of the foot in a very short time period. After using this mode, the physician can go on to the isoscan or single temperature acquisition modes to collect more information about sites of interest.

Figure 5:
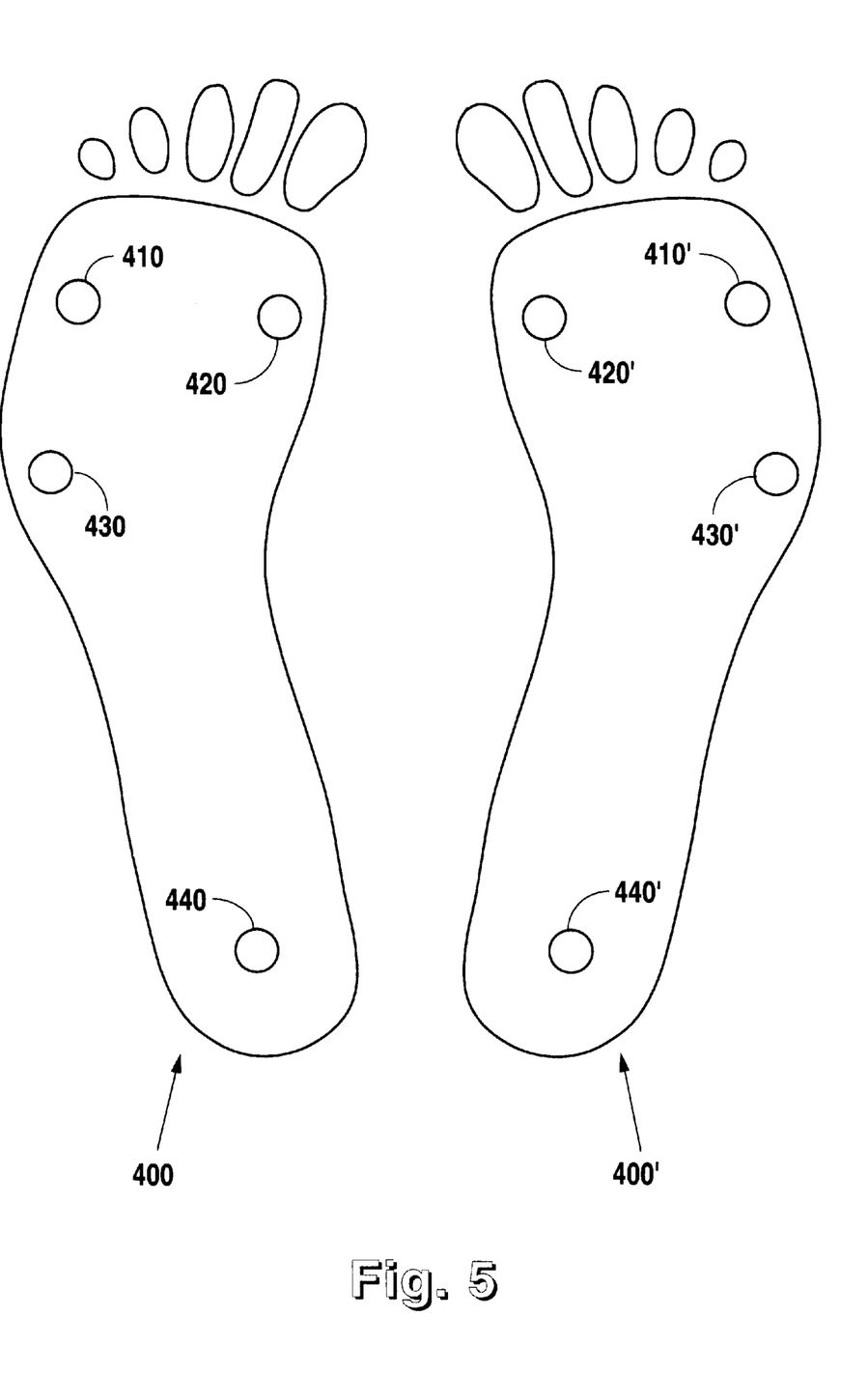
FIG. 5 is a plantar view of the right and left foot, indicating bilateral locations for temperature measurement.

Other features involved in the implementation of the invention can be seen in FIG. 5. In this case, a plantar view of the left and right feet can be seen. The right foot 400 has several numbered sites which correspond to the same sites on the left foot 400'. Each of the numbered locations on the right foot has a corresponding "prime" location on the left foot 400'. That is, right upper lateral sole 410 corresponds to left upper lateral sole 410', the right upper medial sole 420, corresponds to the left upper medial sole 420', the right lateral arch 430 corresponds to left lateral arch 430', and the right heel 440 corresponds to left heel 440'.

The RISKSCAN™ device 300 has the capability of remembering, or storing into the acquisition memory 40 of the controller 20, various temperature readings. This makes it fairly easy for the physician to track (or map for comparison) various suspected locations on the sole of the foot, typically corresponding to pressure points from the metatarsals or other bony prominences of the foot.

In FIG. 5, for example, the physician might decide to map locations on the right foot 400, such as the right upper lateral sole 410, the right upper medial sole 420, the right lateral arch 430, and the right heel 440. These values will be displayed in conjunction with the corresponding locations on the left foot 400': left upper lateral sole 410', left upper medial sole 420', left lateral arch 430', and left heel 440'. Differences of more than 2° C. will be seen as clinically significant and provide early indications to the attending physician as to the condition of the patient's feet. Further, the RISKSCAN™ device 300 may be programmed to display the temperature differentials between corresponding locations, so that a physician may enter location pairs and observe immediately the temperature differences between them.

In addition to the other features described, the apparatus of the invention provides for selective optical barriers to eliminate spurious signals produced by ambient light to the temperature sensor. Disposable templates for use by physicians or patients can be used to consistently locate suspect sites on the sole of the foot for repeatable temperature measurement and evaluation. Further, the physician may select a specific temperature as a "target" or "zero" point for reference, and use this reference for differential readings with respect to the rest of the foot. This particular use of the RISKSCAN™ device 300 may also be selected by way of the mode switch 340. As an adjunct to the variable tones used to indicate variable temperatures at the speaker 120, lights 110 can also be used. For example, a linear array of green, yellow and red LEDs can be used to indicate temperatures near to the target temperature (i.e., green LEDs), temperatures approaching the 2° C. clinical difference (i.e., yellow LEDs), and temperatures above the 2° C. difference (i.e., red LEDs lighted).

Although the present invention is described in terms of preferred exemplary embodiments, other uses of the invention may be obtained from a study of this disclosure and the drawings, along with the appended claims.

What I claim is:

1. A thermometric apparatus for sensing a plurality of temperatures at a dermal surface comprising:
   a controller;
   a timer electrically connected to the controller;
   a memory electrically connected to the controller
   a means for sensing the plurality of temperatures, said temperature sensing means being electrically connected to the controller, said temperature sensing means acting to convert said plurality of temperatures to a corresponding plurality of electrical signals, said controller converting said plurality of electrical signals to a corresponding plurality of temperature numeric values, and said numeric values being stored in the memory;
   a means for sensing proximity to the dermal surface electrically connected to the controller;
   a speaker electrically connected to the controller; and
   a display electrically connected to the controller.

2. The thermometric apparatus of claim 1, wherein the controller and the timer are integrated into a single unit.

3. The thermometric apparatus of claim 1, wherein the controller and the memory are integrated into a single unit.

4. The thermometric apparatus of claim 1, wherein the proximity sensing means comprises a switch activated by capacitance.

5. The thermometric apparatus of claim 1, wherein the temperature sensing means comprises an infrared sensor.

6. The thermometric apparatus of claim 1, wherein the temperature sensing means is inactive until the proximity sensing means senses a predetermined capacitance.

7. The thermometric apparatus of claim 6, wherein the predetermined capacitance is about 10 pF.

8. The thermometric apparatus of claim 1, wherein the display comprises a series of LEDs.

9. The thermometric apparatus of claim 8, wherein the LEDs are arranged in a linear sequence, and selected ones of the LEDs are colored red, yellow, and green.

10. The thermometric apparatus of claim 1, wherein the plurality of temperature numeric values are stored into the memory within a predetermined time period measured by the timer.

11. The thermometric apparatus of claim 10, wherein the predetermined time period is less than about 0.08 seconds.

12. The thermometric apparatus of claim 1, wherein the plurality of temperature numeric values are stored into the memory and averaged by the controller to produce a first average temperature value, said first average temperature value being stored in the memory.

13. The thermometric apparatus of claim 12, wherein the plurality of temperature numeric values are stored into the memory and averaged by the controller to produce a second average temperature value which is compared with the first average temperature value.

14. The thermometric apparatus of claim 13, wherein the second average temperature value is displayed on the display if the difference between the second average temperature value and the first average temperature value is less than a predetermined difference.

15. The thermometric apparatus of claim 14, wherein the predetermined difference is about 0.2° C.

16. The thermometric apparatus of claim 13, wherein the second average temperature value is not displayed on the display if the difference between the second average temperature value and the first average temperature value is greater than a predetermined difference.

17. The thermometric apparatus of claim 16, wherein the predetermined difference is about 0.2° C.

18. The thermometric apparatus of claim 1, wherein the temperature sensing means is electrically connected to the controller using a signal conditioner.

19. The thermometric apparatus of claim 18, wherein the plurality of electrical signals comprise unwanted frequency signals and the signal conditioner operates to filter the plurality of electrical signals by removing the unwanted frequency signals from the plurality of electrical signals.

20. The thermometric apparatus of claim 18, wherein the plurality of electrical signals comprise erratic values and the signal conditioner operates to smooth the plurality of electrical signals by removing the erratic values from the plurality of electrical signals.

21. The thermometric apparatus of claim 18, wherein the plurality of electrical signals comprise noise and the signal conditioner operates to remove the noise from the plurality of electrical signals.

22. The thermometric apparatus of claim 18, wherein the temperature sensing means provides a type k thermocouple output to the signal conditioner.

23. The thermometric apparatus of claim 1, wherein the temperature sensing means and the proximity sensing means are integrated into a single sensor head.

24. The thermometric apparatus of claim 23, wherein the single sensor head is attached to a flexible goose-neck.

25. The thermometric apparatus of claim 1, wherein:

the plurality of temperature numeric values are stored into the memory and averaged by the controller to produce a first average temperature value; and said first average temperature value is displayed on the display.

26. The thermometric apparatus of claim 25, wherein:

the plurality of temperature numeric values are stored into the memory and averaged by the controller to produce a second average temperature value; and the difference between said first average temperature value and said second average temperature value is displayed on the display.

27. The thermometric apparatus of claim 1, wherein the speaker is used to produce an audible tone whose frequency is proportional to the average value of the plurality of numeric values.

28. A method of thermometric diagnosis comprising:

approaching a first bilateral dermal surface with a proximity sensing means until a first proximity signal is detected;

acquiring a first temperature value of said first bilateral dermal surface after said first proximity signal is detected;

approaching a second bilateral dermal surface with the proximity sensing means until a second proximity signal is detected, said second bilateral dermal surface having a one-to-one physical correspondence with said first bilateral dermal surface;

acquiring a second temperature value of said second bilateral dermal surface after said second proximity signal is detected;

subtracting said second temperature value from said first temperature value to produce a temperature difference; and displaying said difference on a display.

29. The method of thermometric diagnosis of claim 28, wherein the steps of:

approaching a first bilateral dermal surface with a proximity sensing means until a first proximity signal is detected;

acquiring a first temperature value of said first bilateral dermal surface after said first proximity signal is detected;

approaching a second bilateral dermal surface with the proximity sensing means until a second proximity signal is detected, said second bilateral dermal surface having a one-to-one physical correspondence with said first bilateral dermal surface;

acquiring a second temperature value of said second bilateral dermal surface after said second proximity signal is detected;

subtracting said second temperature value from said first temperature value to produce a temperature difference; and displaying said difference on a display are performed repeatedly.

30. The method of thermometric diagnosis of claim 28, wherein the first bilateral dermal surface is a selected sole of a first foot, and the second bilateral dermal surface is a selected sole of a second foot.

31. The method of thermometric diagnosis of claim 28 further comprising the step of:
   producing an audible tone whose frequency is proportional to said difference.

32. The method of thermometric diagnosis of claim 28 further comprising the steps of:
   illuminating a green colored visual element when said difference is less than about 2° C.;
   illuminating a yellow colored visual element when said difference is equal to about 2° C.; and
   illuminating a red colored visual element when said difference is greater than about 2° C.

33. A method of thermometric diagnosis comprising the steps of:
   approaching a first dermal surface with a proximity sensing means until a first proximity signal is detected;
   acquiring a first temperature value of said first dermal surface after said first proximity signal is detected;
   displaying said first temperature value on a display;
   approaching a second dermal surface with said proximity sensing means until a second proximity signal is detected;
   acquiring a second temperature value of said second dermal surface after said second proximity signal is detected;
   displaying said second temperature value on said display if said first temperature value is less than said second temperature value; and
   displaying said first temperature value on said display if said temperature value is less than said first temperature value.

34. The method of thermometric diagnosis of claim 33, further comprising the steps of:
   adding a preselected temperature value to said second temperature value to produce a high temperature value;
   subtracting said preselected temperature value from said second temperature value to produce a low temperature value; and
   emitting an audible tone whose frequency is proportional to subsequently acquired temperature values which are greater than said low temperature value and less than said high temperature value.

35. The method of thermometric diagnosis of claim 34, wherein said preselected temperature value is 1.0° C.

* * * * *